(12) United States Patent
Kuechler et al.

(10) Patent No.: US 9,115,068 B2
(45) Date of Patent: Aug. 25, 2015

(54) PROCESSES FOR PRODUCING PHENOL

(75) Inventors: Keith H. Kuechler, Friendswood, TX (US); Francisco M. Benitez, Cypress, TX (US); Kun Wang, Bridgewater, NJ (US); James R. Lattner, LaPorte, TX (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 174 days.

(21) Appl. No.: 13/816,618

(22) PCT Filed: Aug. 16, 2011

(86) PCT No.: PCT/US2011/047848
§ 371 (c)(1),
(2), (4) Date: Apr. 26, 2013

(87) PCT Pub. No.: WO2012/036827
PCT Pub. Date: Mar. 22, 2012

(65) Prior Publication Data
US 2013/0217922 A1    Aug. 22, 2013

Related U.S. Application Data

(60) Provisional application No. 61/382,749, filed on Sep. 14, 2010.

(51) Int. Cl.
| C07C 49/403 | (2006.01) |
| C07C 37/86 | (2006.01) |
| C07C 45/85 | (2006.01) |
| C07C 37/08 | (2006.01) |
| C07C 39/04 | (2006.01) |

(52) U.S. Cl.
CPC .......... *C07C 49/403* (2013.01); *C07C 37/08* (2013.01); *C07C 37/86* (2013.01); *C07C 39/04* (2013.01); *C07C 45/85* (2013.01); *C07C 2101/14* (2013.01)

(58) Field of Classification Search
CPC ........ C07C 37/86; C07C 39/04; C07C 45/85; C07C 49/403; C07C 37/08; C07C 2101/14
USPC ........................................................ 568/798
See application file for complete search history.

(56) References Cited

U.S. PATENT DOCUMENTS

| 3,140,243 A |   | 7/1964 | Feder et al. |
| 3,140,318 A |   | 7/1964 | Sodomann et al. |
| 3,316,302 A |   | 4/1967 | Steeman et al. |
| 3,322,651 A |   | 5/1967 | Nielsen |
| 3,440,525 A | * | 4/1969 | Cardeiro ............ 324/438 |
| 3,442,958 A |   | 5/1969 | Choo |
| 3,692,845 A |   | 9/1972 | Cheema et al. |
| 3,723,514 A | * | 3/1973 | Hegedus et al. ...... 562/446 |
| 3,793,383 A |   | 2/1974 | Johnson et al. |
| 3,933,916 A |   | 1/1976 | Lejeune et al. |
| 4,021,490 A |   | 5/1977 | Hudson |
| 4,122,125 A |   | 10/1978 | Murtha et al. |
| 4,147,726 A | * | 4/1979 | Wu ................. 568/342 |
| 4,282,383 A |   | 8/1981 | Dai et al. |
| 4,298,765 A |   | 11/1981 | Cochran et al. |
| 4,328,372 A |   | 5/1982 | Wu |
| 4,358,618 A |   | 11/1982 | Sifniades et al. |
| 5,064,507 A |   | 11/1991 | O'Donnell et al. |
| 5,066,373 A |   | 11/1991 | Levy et al. |
| 5,254,751 A |   | 10/1993 | Zakoshansky |
| 5,283,376 A |   | 2/1994 | Dyckman et al. |
| 6,037,513 A |   | 3/2000 | Chang et al. |
| 6,201,157 B1 |   | 3/2001 | Keenan |
| 6,388,144 B1 |   | 5/2002 | Wijesekera et al. |
| 6,965,056 B1 |   | 11/2005 | Taggart, II et al. |
| 7,002,048 B2 |   | 2/2006 | Wijesekera et al. |
| 7,205,442 B2 |   | 4/2007 | Payne |
| 7,579,511 B1 |   | 8/2009 | Dakka et al. |
| 2003/0163007 A1 |   | 8/2003 | Dyckman et al. |
| 2006/0211890 A1 |   | 9/2006 | Fodor |
| 2007/0032681 A1 |   | 2/2007 | Walsdorff et al. |

(Continued)

FOREIGN PATENT DOCUMENTS

| WO | 2009/025939 | 2/2009 |
| WO | 2009/058527 | 5/2009 |

(Continued)

OTHER PUBLICATIONS

Baddeley et al., "Relation between Hyperconjugation and COnformation. Part III. Ethyl Alcoholysis of Some Derivatives of Diphenylmethyl Chloride," Journal of the Chemical Society, 1958, 4379-81.*

Werner, "The Preparation of Ethylamine and of Diethylamine," Journal of the Chemical Society, Transactions, 1918, 113, 899-902.*

Schmidt, Robert J., "*Industrial catalytic processes—phenol production*," Applied Catalysis A: General, 2005, vol. 280, p. 89-103.

*Primary Examiner* — Paul A Zucker
*Assistant Examiner* — Mark Luderer
(74) *Attorney, Agent, or Firm* — Siwen Chen; Stephen A. Baehl (57) ABSTRACT

Disclosed herein is a process for producing phenol. The process includes oxidizing at least a portion of a feed comprising cyclohexylbenzene to produce an oxidation composition comprising cyclohexyl-1-phenyl-1-hydroperoxide. The oxidation composition may then be cleaved in the presence of an acid catalyst to produce a cleavage reaction mixture comprising the acid catalyst, phenol and cyclohexanone. At least a portion of the cleavage reaction mixture may be neutralized with a basic material to form a treated cleavage reaction mixture. In various embodiments, the treated cleavage reaction mixture contains no greater than 50 wppm of the acid catalyst or no greater than 50 wppm of the basic material.

16 Claims, 1 Drawing Sheet

(56) References Cited

U.S. PATENT DOCUMENTS

| | | |
|---|---|---|
| 2007/0276156 A1 | 11/2007 | Matsumura et al. |
| 2011/0037022 A1 | 2/2011 | Dakka et al. |
| 2011/0105805 A1 | 5/2011 | Buchanan et al. |
| 2011/0301387 A1 | 12/2011 | Wang et al. |

FOREIGN PATENT DOCUMENTS

| | | |
|---|---|---|
| WO | 2009/058531 | 5/2009 |
| WO | 2009/128984 | 10/2009 |

\* cited by examiner

PROCESSES FOR PRODUCING PHENOL

PRIORITY CLAIM

This application is a National Stage Application of International Application No. PCT/US2011/047848 filed Aug. 16, 2011, which claims priority to and the benefit of U.S. Provisional Application Serial No. 61/382,749, which was filed Sep. 14, 2010, and is incorporated herein by reference in its entirety.

CROSS REFERENCE TO RELATED APPLICATIONS

This application is related to U.S. Provisional Application Serial Nos. 61/382,788; 61/382,776; PCT Application Nos. PCT/US2011/047829; and PCT/US2011/047834.

FIELD

The present invention relates to a process for producing phenol.

BACKGROUND

Phenol is most commonly produced by the Hock process. The Hock process involves alkylation of benzene with propylene to produce cumene, oxidation of the cumene to the corresponding hydroperoxide, and cleavage of the hydroperoxide to produce equimolar amounts of phenol and acetone.

Phenol can also be produced from cyclohexylbenzene. For example, cyclohexylbenzene can be produced by direct alkylation of benzene with cyclohexene, or, as disclosed in U.S. Pat. No. 6,037,513, by contacting benzene with hydrogen in the presence of a catalyst. The cyclohexylbenzene can then be oxidized to the corresponding hydroperoxide, and the hydroperoxide decomposed to phenol and cyclohexanone using an acid catalyst. The acidic catalyst will be present in the cleavage reaction mixture, and may cause corrosive damage to the process equipment, and/or may cause unwanted reactions in the downstream processing steps (e.g., separations and purifications).

U.S. Pat. No. 6,201,157 ('157 Patent) generally relates to a method for producing phenol and acetone by decomposition of cumene hydroperoxide in the presence of an acid catalyst, wherein the acid catalyst is neutralized after substantial completion of the decomposition by addition of a substituted amine. The '157 Patent directs one to use highly hindered amines, particularly aromatic amines, in a desire to enable treatment of the acid catalyst at a high temperature without consuming the amine in a byproduct reaction with acetone. The '157 Patent, and many others concerned with production of phenol starting from cumene hydroperoxide, directs one to use quite low amounts of acid catalyst (e.g., 34-38 ppm sulfuric acid), ostensibly to minimize the potential consumption of valuable acetone co-product from undesirable byproduct reactions.

The inventors have discovered that there are many differences between the manufacture of phenol starting from cumene as provided in the literature, and that starting from cyclohexylbenzene. While many of the objectives of the two processes are similar, for example initiating a cleavage reaction with an acid while minimizing undesirable byproduct reactions, the means of accomplishing them are quite different by virtue of the substantially different stream compositions and processing steps.

The instant invention sets out methods of producing phenol starting from cyclohexyl-1-phenyl-1-hydroperoxide that go in a much different direction than the cumene literature. These include, for example, finding advantageous performance in higher levels of acid catalyst in the cleavage reaction, and lower temperatures and the use of aliphatic amines in the treatment reaction, correlated to the unique compositions in these reactions when starting from cyclohexylbenzene.

SUMMARY

The invention relates to a process for producing phenol comprising: (a) oxidizing at least a portion of a feed comprising cyclohexylbenzene to produce an oxidation composition comprising cyclohexyl-1-phenyl-1-hydroperoxide; (b) cleaving at least a portion of the oxidation composition in the presence of an acid catalyst to produce a cleavage reaction mixture comprising the acid catalyst, phenol and cyclohexanone; and (c) neutralizing at least a portion of the cleavage reaction mixture with a basic material to form a treated cleavage reaction mixture, wherein the treated cleavage reaction mixture contains no greater than 50 wppm of the acid catalyst and/or no greater than 50 wppm of the basic material.

In one embodiment, the oxidation composition further comprises at least 65 wt % cyclohexylbenzene, the wt % based upon the total weight of the oxidation composition. In addition, the oxidation composition may further comprise one or more hydroperoxides selected from cyclohexyl-1-phenyl-2-hydroperoxide; cyclohexyl-1-phenyl-3-hydroperoxide; cyclohexyl-1-phenyl-4-hydroperoxide; cyclopentyl-1-methyl-2-phenyl-2-hydroperoxide; cyclopentyl-1-methyl-3-phenyl-3-hydroperoxide; cyclopentyl-1-methyl-1-phenyl-2-hydroperoxide; cyclopentyl-1-methyl-1-phenyl-3-hydroperoxide; cyclohexyl-1-phenyl-1,2-dihydroperoxide; cyclohexyl-1-phenyl-1,3-dihydroperoxide; cyclohexyl-1-phenyl-1,4-dihydroperoxide; cyclopentyl-1-methyl-2-phenyl-1,2-dihydroperoxide; cyclopentyl-1-methyl-2-phenyl-2,3-dihydroperoxide; cyclopentyl-1-methyl-2-phenyl-2,4-dihydroperoxide; and cyclopentyl-1-methyl-2-phenyl-2,5-dihydroperoxide.

Conveniently, the acid catalyst is one or more of sulfuric acid, perchloric acid, phosphoric acid, hydrochloric acid and p-toluene sulfonic acid. The cleavage reaction mixture may contain at least 50 weight-parts-per-million (wppm) and no greater than 5000 wppm of the acid catalyst, based upon total weight of the cleavage reaction mixture.

In certain aspects of the process, the basic material is one or more of ammonia, ammonium hydroxide, an alkali metal hydroxide, a basic clay, an anionic exchange resin, an activated carbon or an amine, such as an aliphatic amine or a diamine.

Other specific embodiments include a neutralization reaction that occurs at a temperature of at least 30° C. and no greater than 200° C., and a pressure of at least 5 and no greater than 3450 kPa, such as a temperature of at least 40° C. and no greater than 150° C. and a pressure of at least 70 kPa and no greater than 1380 kPa, including a temperature of at least 50° C. and no greater than 110° C. and a pressure of at least 70 kPa and no greater than 1380 kPa.

In various manifestations of the invention, the treated cleavage reaction mixture contains no greater than 50 wppm of the acid catalyst and/or no greater than 50 wppm of the basic material, or no greater than 25 wppm of the acid catalyst and no greater than 25 wppm of the basic material. The amount of acid catalyst or basic material in the treated cleavage reaction mixture may be determined using a calibrated method. A calibrated method is a conventional pH method further developed to correlate the reading that conventional pH method or instrument may provide to a given amount of acid catalyst or basic material content in an organic matrix based on the specific acid catalyst, basic material and organic matrix being employed in the present invention. The invention may further include that the amount of acid catalyst or basic material in the treated cleavage reaction mixture is determined continually using the calibrated method, and continually determining a difference between the continually determined amount of acid catalyst or basic material and a target amount of acid catalyst or basic material in the treated cleavage reaction mixture, and adjusting the amount of basic material on the basis of the continually determined difference to approach the target amount of acid catalyst or basic material in the treated cleavage reaction mixture.

In another particular aspect, the neutralization reaction of the basic material and acid catalyst forms a complexation product that is soluble in the treated cleavage reaction mixture, is stable at a temperature of at least 185° C., and has a lower volatility than cyclohexylbenzene. Conveniently, at least a portion of the treated cleavage reaction mixture is subjected to one or more fractional distillation steps to produce a bottoms material that comprises no greater than 5 wt % of cyclohexylbenzene, phenol and cyclohexanone combined, that wt % being based on the total weight of the bottoms material, and further contains at least 95 wt % of the complexation product contained in the at least a portion of the treated cleavage reaction mixture subjected to fractional distillation, that wt % based upon the total weight of the at least a portion of the treated cleavage reaction mixture subjected to fractional distillation.

In various embodiments, all or a portion of the feed comprising cyclohexylbenzene may be formed by alkylating or hydroalkylating benzene.

DETAILED DESCRIPTION

Various specific embodiments, versions and examples of the invention will now be described, and definitions adopted herein for purposes of understanding the claimed invention. While the following detailed description may provide specific embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more of the inventions defined by the claims.

Production of the Cyclohexylbenzene

In a process for producing phenol and cyclohexanone from benzene, the benzene is initially converted to cyclohexylbenzene by any conventional technique, including alkylation of benzene with cyclohexene in the presence of an acid catalyst, such as zeolite beta or an MCM-22 family molecular sieve, or by oxidative coupling of benzene to make biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

For an example of hydroalkylation of benzene in the presence of hydrogen for the production of cyclohexylbenzene, see U.S. Pat. Nos. 6,730,625 and 7,579,511 which are incorporated by reference. Also, see International Applications WO2009131769 or WO2009128984 directed to catalytic hydroalkylation of benzene in the presence of hydrogen for the production of cyclohexylbenzene.

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves having the MWW framework topology. (Such crystal structures are discussed in the "Atlas of Zeolite Framework Types", Fifth edition, 2001, the entire content of which is incorporated as reference).

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954, 325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction is highly selective towards cyclohexylbenzene, the effluent from the hydroalkylation reaction will normally contain some dialkylated products, as well as unreacted benzene and the desired monoalkylated species. The unreacted benzene is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

After removal of the unreacted benzene and the polyalkylated benzenes and other heavy species, the cyclohexylbenzene is fed to the oxidation reaction. Typically, however, this cyclohexylbenzene feed contains the following contaminants generated as by-products of its synthesis:
  between 1 wppm and 1 wt % bicyclohexane, or between 10 wppm and 8000 wppm bicyclohexane;
  between 1 wppm and 1 wt % biphenyl, or between 10 wppm and 8000 wppm biphenyl;
  between 1 wppm and 2 wt % methylcyclopentylbenzene, or between 10 wppm and 1 w % wppm methylcyclopentylbenzene as any isomer: 1-phenyl-1-methylcyclopentane, 1-phenyl-2-methylcyclopentane, and 1-phenyl-3-methylcyclopentane; and
  less than about 1000 wppm, such as less than 100 wppm of phenol, olefins or alkylene benzenes, such as cyclohexenyl benzene.

Oxidation Reaction

As discussed above, the process includes oxidizing at least a portion of a feed comprising cyclohexylbenzene to produce an oxidation composition comprising cyclohexyl-1-phenyl-1-hydroperoxide. As used herein, "oxidizing" means causing an oxidation reaction to occur.

The feed comprising cyclohexylbenzene may be produced by any process known to those in the art, and while desirably pure, may contain a small amount of certain byproduct components that are difficult to remove from cyclohexylbenzene, discussed later. The hydroalkylation process may generate byproduct dicyclohexylbenzene, and thus be accompanied by and integrated with the transalkylation of byproduct dicyclohexylbenzene with benzene to produce additional cyclohexylbenzene, and may further include various separations to recover and recycle unreacted benzene, and remove heavy alkylates and other unselective byproducts. Another known method to manufacture a feed comprising cyclohexylbenzene involves the catalytic alkylation of benzene with cyclohexene.

Further, in an embodiment, a portion of the feed comprising cyclohexylbenzene may be a recycle stream comprising cyclohexylbenzene produced by the processing of the treated cleavage reaction mixture, discussed later. In this manner, all or a fraction of cyclohexylbenzene that was unreacted in the oxidation reaction may be recovered and reused to generate additional phenol.

Regardless of the source or sources, in various embodiments, a feed comprising cyclohexylbenzene contains at least about 10 wt %, or at least about 25 wt %, or at least about 50 wt %, or at least about 65 wt %, or at least about 75 wt %, or at least about 95 wt %, or at least about 99 wt % cyclohexylbenzene. In various embodiments, it may contain another component. For example, the feed comprising cyclohexylbenzene may contain at least 1 wppm and no greater than 1 wt % bicyclohexane, or at least 10 wppm and no greater than 8000 wppm bicyclohexane. It may contain at least 1 wppm and no greater than 1 wt % biphenyl, or at least 10 wppm and no greater than 8000 wppm biphenyl. It may contain at least 1 wppm and no greater than 2 wt % methylcyclopentylbenzene, or at least 10 wppm and no greater than 1 wt % methylcyclopentylbenzene as any isomer: 1-phenyl-1-methylcyclopentane, 1-phenyl-2-methylcyclopentane, and 1-phenyl-3-methylcyclopentane. There may be other components present, though desirably of low concentration, say, no greater than 1000 wppm, or no greater than 100 wppm of phenol, olefins or alkylene benzenes such as cyclohexenyl benzene, individually or in any combination. For example, in various embodiments, all or a portion of the feed may be subjected to a hydrogenation reaction to hydrogenate at least a portion of one or more of the phenol, olefins and/or alkylene benzenes. The feed comprising cyclohexylbenzene to which oxygen is introduced to cause an oxidation reaction may contain cyclohexylbenzene and any other one component, or any combination of the other components just noted in the proportions for each or in combination just noted.

In various exemplary embodiments, oxidation may be accomplished by contacting oxygen, e.g., (an oxygen-containing gas, such as air and various derivatives of air), with a feed comprising cyclohexylbenzene. For example, one may use air that has been compressed and filtered to removed particulates, air that has been compressed and cooled to condense and remove water, or air that has been enriched in oxygen above the natural approximately 21 mol % in air through membrane enrichment of air, cryogenic separation of air or other means within the ken of the skilled artisan.

The oxidation may be conducted in the absence or presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N''-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount between 0.0001 wt % to 15 wt %, such as between 0.001 wt % to 5 wt %, of the cyclohexylbenzene.

In various embodiments, the oxidation reaction occurs under oxidation conditions. Suitable oxidation conditions include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

Typically, the product of the oxidation of a feed comprising cyclohexylbenzene, i.e., the oxidation composition, contains at least 5 wt %, such as at least 10 wt %, for example at least 15 wt %, or at least 20 wt % cyclohexyl-1-phenyl-1-hydroperoxide based upon the total weight of the oxidation composition. In other manifestations, the oxidation composition contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation composition. The oxidation composition may further comprise imide catalyst and unreacted cyclohexylbenzene. The invention may include cyclohexylbenzene in the oxidation composition in an amount of at least 50 wt %, or at least 60 wt %, or at least 65 wt %, or at least 70 wt %, or at least 80 wt %, or at least 90 wt %, based upon total weight of the oxidation composition.

In addition, the oxidation composition may contain one or more hydroperoxides other than cyclohexyl-1-phenyl-1-hydroperoxide generated as a byproduct of the oxidation reaction of cyclohexylbenzene, or as the oxidation product of some oxidizable component other than cyclohexylbenzene that may have been contained in the cyclohexylbenzene undergoing oxidation. Such oxidizable components include methylcyclopentylbenzenes of various isomers, and bicyclohexane. Exemplary other hydroperoxides present in the oxidation composition include at least, based on the total weight of the oxidation composition, 0.1 wt % to no greater than 10 wt %, or at least 0.5 wt % to no greater than 5.0 wt %, or at least 1 wt % and no greater than 4 wt % of any one or any combination of: cyclohexyl-1-phenyl-2-hydroperoxide; cyclohexyl-1-phenyl-3-hydroperoxide; cyclohexyl-1-phenyl-4-hydroperoxide; cyclopentyl-1-methyl-2-phenyl-2-hydroperoxide; cyclopentyl-1-methyl-3-phenyl-3-hydroperoxide; cyclopentyl-1-methyl-1-phenyl-2-hydroperoxide; cyclopentyl-1-methyl-1-phenyl-3-hydroperoxide; cyclohexyl-1-phenyl-1,2-dihydroperoxide; cyclohexyl-1-phenyl-1,3-dihydroperoxide; cyclohexyl-1-phenyl-1,4-dihydroperoxide; cyclopentyl-1-methyl-2-phenyl-1,2-dihydroperoxide; cyclopentyl-1-methyl-2-phenyl-2,3-dihydroperoxide; cyclopentyl-1-methyl-2-phenyl-2,4-dihydroperoxide; and cyclopentyl-1-methyl-2-phenyl-2,5-dihydroperoxide.

The reactor used for the oxidation of cyclohexylbenzene, i.e., the oxidation reactor, may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel container with a distributor inlet for the oxygen-containing stream in line. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner well known to those skilled in the art.

At least a portion of the oxidation composition may be subjected to a cleavage reaction, which may include all or some fraction of the oxidation composition as directly produced without undergoing any separation (e.g., some fraction resulting from diverting some amount of the oxidation composition as directly produced to another disposition, such as temporary storage). Thus, the at least a portion of the oxidation composition may have the same composition as the oxidation composition. Further, all or some of the oxidation composition as directly produced may undergo one or more separations, and an appropriate product of that separation (or separations), now modified in composition relative the oxidation composition as directly produced, may provide the at least a portion of the oxidation composition subjected to the cleavage reaction.

For example, all or a fraction of the oxidation composition as directly produced may be subjected to high vacuum distillation, to generate a product enriched in unreacted cyclohexylbenzene, and the at least a portion of the oxidation composition as a residue concentrated in the desired cyclohexyl-1-phenyl-1-hydroperoxide that may be subjected to a cleavage reaction. Cyclohexylbenzene is essentially a diluent in the cleavage reaction and the neutralization reaction, and further is not a good solvent for most acid catalysts, particularly sulfuric acid. However, distinctive from the Hock process described earlier, it is convenient in the present invention that the at least a portion of the oxidation composition that will undergo the cleavage reaction be of the same composition of cyclohexylbenzene as the oxidation composition directly produced. That is to say, it is convenient that the at least a portion of the oxidation composition undergo no concentration of the hydroperoxide(s) before the acid catalyst is introduced to it, because the starting alkylbenzene cyclohexylbenzene has a significantly higher normal boiling point than the starting alkylbenzene cumene that is found in the Hock process. While within the scope of the present invention, any practical separation attempted to concentrate the cyclohexyl-1-phenyl-1-hydroperoxide or other hydroperoxides from cyclohexylbenzene prior to effecting the cleavage reaction likely requires inconvenient very low vacuum pressure distillation equipment, and even then likely requires very high temperatures that could cause dangerous, uncontrolled thermal decomposition of the hydroperoxides.

Additionally or alternatively, all or a fraction of the oxidation composition, or all or a fraction of the vacuum distillation residue may be cooled to cause crystallization of the unreacted imide oxidation catalyst, which can then be separated either by filtration or by scraping from a heat exchanger surface used to effect the crystallization, and provide an at least a portion of the oxidation composition reduced or free from imide oxidation catalyst that may be subjected to a cleavage reaction.

As another example, all or a fraction of the oxidation composition as produced may be subjected to water washing and then passage through an adsorbent, such as a 3 A molecular sieve, to separate water and other adsorbable compounds, and provide an at least a portion of the oxidation composition with reduced water or imide content that may be subjected to a cleavage reaction. Similarly, all or a fraction of the oxidation composition may undergo a chemically or physically based adsorption, such as passage over a bed of sodium carbonate to remove the imide oxidation catalyst (e.g., NHPI) or other adsorbable components, and provide at least a portion of the oxidation composition reduced in oxidation catalyst or other adsorbable component content that may be subjected to a cleavage reaction. Another possible separation involves contacting all or a fraction of the oxidation composition as produced with a liquid containing a base, such as an aqueous solution of an alkali metal carbonate or hydrogen carbonate, to form an aqueous phase comprising a salt of the imide oxidation catalyst, and an organic phase reduced in imide oxidation catalyst provided as an at least a portion of the oxidation composition that may be subjected to a cleavage reaction. An example of separation by basic material treatment is disclosed in International Application No. WO2009/025939.

Cleavage Reaction

As discussed above, the process includes cleaving at least a portion of the oxidation composition in the presence of an acid catalyst to produce a cleavage reaction mixture comprising the acid catalyst, phenol and cyclohexanone. As used herein, "cleaving" means causing a cleavage reaction to occur. In the cleavage reaction, at least a portion of the desired cyclohexyl-1-phenyl-1-hydroperoxide will decompose in high selectivity to cyclohexanone and phenol, and further, any other hydroperoxides present will decompose to various products, discussed below.

In various embodiments, the acid catalyst is at least partially soluble in the cleavage reaction mixture, stable at a temperature of at least 185° C. and has a lower volatility (higher normal boiling point) than cyclohexylbenzene. In various embodiments, the acid catalyst is also at least partially soluble in the treated cleavage reaction mixture.

Acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In various embodiments of the present invention, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

As a result of potentially high amounts of cyclohexylbenzene in the cleavage reaction mixture, considerably higher than cumene in the Hock process material undergoing a cleavage reaction, it may be convenient in the present invention to use more acid catalyst to effect the cleavage reaction than typically believed optimal in the Hock process, to at least partially overcome the insolubility of the acid in the cleavage reaction mixture. However, lower amounts of acid catalyst may be applied in the present invention, with appropriate additional cleavage reactor volume and residence time of the cleavage reaction mixture in the cleavage reactor to obtain high hydroperoxide conversion.

In various embodiments, the cleavage reaction occurs under cleavage conditions. Suitable cleavage conditions include a temperature of at least 20° C. and no greater than 200° C., or at least 40° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

Conversion of any hydroperoxide, such as cyclohexyl-1-phenyl-1-hydroperoxide, and conveniently all cyclohexyl-1-phenyl-1-hydroperoxide and other hydroperoxides, is generally very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given specie of hydroperoxide, or of all cyclohexyl-1-phenyl-1-hydroperoxide and other hydroperoxides present in the at least a portion of the oxidation composition undergoing the cleavage reaction. This is desirable because any hydroperoxide, even the cyclohexyl-1-phenyl-1-hydroperoxide, becomes a contaminant in the cleavage reaction mixture and treated cleavage reaction mixture, discussed below. Hydroperoxides cause undesired chemistry when decomposed under uncontrolled conditions outside the cleavage reaction, for if thermally decomposed under the conditions in a distillation column.

The major products of the cleavage reaction of cyclohexyl-1-phenyl-1-hydroperoxide are phenol and cyclohexanone, each of which generally comprise about 40 to about 60 wt %, or about 45 to about 55 wt % of the cleavage reaction mixture, such wt % based on the weight of the cleavage reaction mixture exclusive of unreacted cyclohexylbenzene and acid catalyst.

The cleavage reaction mixture may comprise no greater than 30 wt %, or no greater than 25 wt %, or no greater than about 15 wt % of phenol, or it may comprise at least 1 wt %, or at least 3 wt %, or at least 5 wt %, or at least 10 wt % phenol, based on total weight of the cleavage reaction mixture. Further, the cleavage reaction mixture may comprise no greater than 30 wt %, or no greater than 25 wt %, or no greater than about 15 wt % of cyclohexanone, or it may comprise at least 1 wt %, or at least 3 wt %, or at least 5 wt %, or at least 10 wt % cyclohexanone, based on total weight of the cleavage reaction mixture.

The cleavage reaction mixture may further comprise at least 0.1 and no greater than 10 wt %, or at least 0.5 and no greater than 7 wt %, or at least 1 and no greater than 5 wt %, or at least 1.5 and no greater than 3 wt % of any one or combination of contaminant byproducts based on the total weight of the cleavage reaction mixture.

As used herein, a "contaminant" or a "contaminant byproduct" may include any unwanted hydrocarbon or oxygenated hydrocarbon component in the cleavage reaction mixture or the neutralized cleavage mixture, or any portion of either; that is anything other than phenol, cyclohexanone and cyclohexybenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage reaction mixture or the neutralized cleavage mixture or any portion thereof may have been produced in any element of the present invention, or may have been contained in the feed comprising cyclohexylbenzene undergoing oxidation. For example, a contaminant may be present in the cleavage reaction mixture as a result of one or more of: (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation composition from (ii).

Examples of contaminants in the cleavage reaction mixture, and possible amounts thereof, include (weight-parts-per-million (wppm) and wt % are based upon total weight of the cleavage reaction mixture):

water, e.g., at least 100 wppm and no greater than 3.0 wt %;

twelve carbon, two ringed hydrocarbons other than cyclohexylbenzene, such as bicyclohexane, cyclohexenylcyclohexane, and cyclohexadienylcyclohexane, cyclohexenylbenzene, cyclohexadienylbenzene and biphenyl, e.g at least 10 wppm and no greater than 3.0 wt %, each or in total;

saturated and unsaturated ketones, such as pentanones, methylcyclopentanones, hexanones, 1-phenylhexan-1-one and 1-cyclohexylhexan-1-one, phenylcyclohexanones and phenylmethylcyclopentanones, e.g., at least 10 wppm and no greater than 4.0 wt %, each or in total;

cyclohexyldione(s), e.g., at least 10 wppm and no greater than 1.0 wt % in total;

less than 12 carbon, unsaturated hydrocarbons, cyclic and acyclic, or combinations thereof, such as cyclohexene, e.g., at least 10 wppm and no greater than 1.0 wt %, each or in total;

cyclohexanol, e.g., at least 10 wppm and no greater than 1.0 wt %;

cyclohexenone(s), e.g., 2-cyclohexenone or 3-cyclohexenone, e.g., at least 10 wppm and no greater than 2.0 wt %, each or in total;

hydroxycyclohexanone(s), e.g., at least 10 wppm and no greater than 2.0 wt % in total;

carboxylic acids, such as benzoic acid, e.g., at least 10 wppm and no greater than 1.0 wt %, each or in total;

phenyl cyclohexanol(s), e.g., 1-phenylcyclohexan-1-ol, 2-phenylcyclohexan-1-ol, 3-phenylcyclohexan-1-ol and 4-phenylcyclohexan-1-ol, e.g., at least about 10 wppm and no greater than 5.0 wt %, each or in total;

cyclohexyl cyclohexanol(s), such as 1-cyclohexylcyclohexan-1-ol, 2-cyclohexylcyclohexan-1-ol, 3-cyclohexylcyclohexan-1-ol, and 4-cyclohexylcyclohexan-1-ol, e.g., at least 10 wppm and no greater than 1.0 wt %, each or in total;

unsaturated alkyl oxygenated cyclohexanes, such as cyclohexenyl cyclohexanols and cyclohexenyl cyclohexanones, and methylcyclopentenyl cyclohexanols and methylcyclopentenyl cyclohexanones, e.g., at least 10 wppm and no greater than 1.0 wt %, each or in total;

aldehydes, especially, pentanals, hexanals, cyclohexyl or methylcyclopentyl alkyl aldehydes, such 5-cyclohexyl hexanal, and 6-hydoxy-5-cyclohexyl hexanal, e.g., at least 10 wppm and no greater than 1.0 wt %, each or in total;

1-phenyl-6-hydroxyhexan-1-one (also called 6-hydroxyhexanophenone), e.g., at least 10 wppm and no greater than 4.0 wt %;

1-cyclohexyl-6-hydroxyhexan-1-one, e.g., at least 10 wppm and no greater than 1.0 wt %;

benzoic esters, e.g., at least 10 wppm and no greater than 1.0 wt %, each or in total; and a hydroperoxide (e.g., an unreacted hydroperoxide). Non-limiting examples include: the desired cyclohexyl-1-phenyl-1-hydroperoxide, and the other hydroperoxides such as cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, cyclopentyl-1-methyl-2-phenyl-2,5-dihydroperoxide; e.g., at least 1 wppm and no greater than 1.0 wt %, each or in total.

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

At least a portion of the cleavage reaction mixture may be subjected to a neutralization reaction, which may include all or some fraction of the cleavage reaction mixture as directly produced without undergoing any separation (e.g., some fraction resulting from diverting some amount of the cleavage reaction mixture as directly produced to another disposition, such as temporary storage). Thus, the at least a portion of the cleavage reaction mixture may have the same composition as the cleavage reaction mixture. Further, all or some of the cleavage reaction mixture as directly produced may undergo one or more separations, and an appropriate product of that separation (or separations), now modified in composition relative the cleavage reaction mixture as directly produced, may provide the at least a portion of the cleavage reaction mixture subjected to the neutralization reaction.

Neutralization Reaction

As discussed above, the process further includes neutralizing at least a portion of the cleavage reaction mixture with a basic material to form a treated cleavage reaction mixture. In various embodiments, "neutralizing" means causing a neutralization reaction to occur.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to distill in the bottoms product in subsequent fractionation operations that may be conducted on the least a portion of the treated cleavage reaction mixture that may contain such liquid basic material.

In one embodiment, the basic material has an ionization constant of greater than about $8.6 \times 10^{-5}$ measured at 25° C.

The conditions at which the neutralization reaction is effected, or neutralization conditions, vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. Further, the neutralization condition temperature may be in any range of the aforementioned temperatures. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

The treated cleavage reaction mixture may include cyclohexylbenzene in an amount of at least 50 wt %, or at least 60 wt %, or at least 65 wt %, or at least 70 wt %, or at least 80 wt %, or at least 90 wt %, based upon total weight of the treated cleavage reaction mixture.

The treated cleavage reaction mixture may further comprise at least 0.1 and no greater than 10 wt %, or at least 0.5 and no greater than 7 wt %, or at least 1 and no greater than 5 wt %, or at least 1.5 and no greater than 3 wt % of any one or combination of contaminant byproducts based on the total weight of the cleavage reaction mixture. Example contaminant byproducts and their possible amounts in the treated cleavage reaction mixture are the same as discussed in detail above for the cleavage reaction mixture. In general, a contaminant byproduct in the cleavage reaction mixture will not undergo significant conversion in the neutralization reaction.

In various exemplary embodiments, the neutralization reaction results in the formation of a complexation product, such as an acid-basic material salt. For example, when sulfuric acid is the acid catalyst:

using sodium hydroxide as the basic material, water, and a salt of sodium sulfate, Na$_2$SO$_4$, is formed that is not soluble in the treated cleavage reaction mixture;

using methylamine as the basic material, a complex of (CH$_3$NH$_2$)$_2$.H$_2$SO$_4$ is formed, among other possible complexes, that may be soluble in the treated cleavage reaction mixture; and using hexamethylenediamine as the basic material, complexes of $(H_2N(CH_2)_6NH_2)_2 \cdot H_2SO_4$, among other possible complexes, are formed that are soluble in the treated cleavage reaction mixture.

Conveniently, the complexation product is soluble in the treated cleavage reaction mixture and will stay in the bottoms products of subsequent distillations of at least a portion of the treated cleavage reaction mixture, thus eliminating the need for additional separations to remove the complexation product from the at least a portion of the treated cleavage reaction mixture.

Conveniently, the complexation product has a low volatility, with a normal boiling point above phenol or cyclohexylbenzene, such that it will tend to distill in the bottoms product of subsequent fractionation operations that may be conducted on the at least a portion of the treated cleavage reaction mixture containing the complexation product.

Conveniently, the complexation product has a high thermal stability and does not dissociate or otherwise decompose at high temperatures associated with subsequent processing of the neutralized cleavage product, particularly distillation, such as at least about 300° C., or at least about 275° C., or at least about 250° C., or at least about 225° C., or at least about 200° C.

The complexation product may be substantially inert to the other components in the treated cleavage reaction mixture or other streams derived therefrom, such as cyclohexanone, phenol, cyclohexylbenzene, contaminants and/or mixtures thereof.

When basic material is introduced to the at least a portion of the cleavage reaction mixture and the neutralization reaction occurs, some or all of acid catalyst and basic material are transformed to complexation product. Introducing basic material at a point prior to perfect stoichiometric complexation or reaction (i.e., acid catalyst is still the excess reactant), the treated cleavage reaction mixture will have a reduced content of acid catalyst relative to the at least a portion of the cleavage reaction mixture undergoing the neutralization reaction, and a low content of basic material, potentially none. Introducing basic material at just the point of perfect stoichiometric complexation or reaction, the treated cleavage reaction mixture will have a very low content of acid catalyst relative to the at least a portion of the cleavage reaction product, potentially none, and also a very low content of basic material, potentially none. Introducing basic material past the point of perfect stoichiometric complexation or reaction (i.e., basic material is now the excess reactant), the treated cleavage reaction mixture will have a reduced content of acid catalyst relative to the at least a portion of the cleavage reaction product, potentially none, but will have a content of basic material increasing in proportion to the amount of basic material introduced. As noted earlier, a complexation product, though potentially comprising each acid catalyst and basic material specie, is neutralized and generally inert. An uncomplexed specie, or unreacted specie in the case of a more definitive reaction such as sodium hydroxide with sulfuric acid, is capable of undergoing or catalyzing various types of chemistry, desired and undesired. Further, it is possible that both the acid catalyst and the basic material are present in the treated cleavage reaction mixture, even with one or the other in excess of stoichiometry, due to imperfect mixing in or insufficient residence time of the cleavage reaction.

In various embodiments, basic material is introduced to the at least a portion of the cleavage reaction mixture to form a treated cleavage reaction mixture that contains no greater than 150 wppm of the acid catalyst, or no greater than 100 wppm, or no greater than 50 wppm, or no greater than 25 wppm, or no greater than 10 wppm, or no greater than 2 wppm of the acid catalyst, based upon total weight of the treated cleavage reaction mixture. Additionally or alternatively, basic material is introduced to the at least a portion of the cleavage reaction mixture to form a treated cleavage reaction mixture that contains no greater than 150 wppm of the basic medium, or no greater than 100 wppm, or no greater than 50 wppm, or no greater than 25 wppm, or no greater than 10 wppm, or no greater than 2 wppm of the basic medium, based upon total weight of the treated mixture. Lower contents of both acid catalyst and basic material in the treated cleavage reaction mixture are desirable, as either constituent will cause adverse reactions of the desired cyclohexanone and phenol products in subsequent separation and purification operations using at least a portion of the treated cleavage reaction mixture, particularly in distillation columns.

The amount of basic material introduced to the at least a portion of the cleavage reaction mixture to obtain a given level of acid catalyst or basic material in the neutralized cleavage reaction product is highly dependent on and varies widely with both the acid catalyst and the basic material selected, and, of course, the amount of acid catalyst in the at least a portion of the cleavage reaction mixture.

Further, the techniques for measurement of the amount of basic material or acid catalyst in a largely or exclusively organic matrix such as a treated cleavage reaction mixture are also quite specific to both the acid catalyst and the basic material selected, and the nature of the organic matrix. The typical method for such measurement in aqueous systems is the determination of a pH value using various methods, as the classical definition of pH is related to hydrogen ion activity in a highly aqueous matrix. Conventional methods of and instruments used in the determination of pH are based on a highly aqueous matrix, and the pH value they provide on hydrogen ion activity is directly related and converted to acid or base concentration in the aqueous matrix. However, while such conventional pH methods and instruments may provide pH readings for an organic matrix, such readings cannot be readily related or converted to acid or base concentration as they are in an aqueous matrix.

To overcome this problem of the measurement of the amount of basic material or acid catalyst in a largely or exclusively organic matrix such as a treated cleavage reaction mixture, one may employ what is herein termed a "calibrated method." A calibrated method is a conventional pH method further developed to correlate the reading that conventional pH method or instrument may provide to a given amount of acid catalyst or basic material content in an organic matrix based on the specific acid catalyst, basic material and organic matrix of interest.

Two fundamental approaches are available to develop calibrated methods for organic matrices based on conventional pH methods and instruments, and thus determine the acid catalyst and basic material concentration in an organic matrix such as a treated cleavage reaction mixture. The first involves dilution of an aliquot of the organic matrix in a large quantity of a highly hydrogen bonded composition, generally including water or an alcohol, or both. For example, in the pH measurement of phenol for use in DNA experiments in the biochemical industry, a reported method includes mixing 2 ml of the organic phase with 5 ml of methanol and 13 ml of water, then measuring the pH of the entire sample. The pH measurement thereby obtained has been correlated to some property of the undiluted phenol matrix, such as the ability of the phenol to have DNA to partition into the organic, phenolic phase. This is assigned in the biochemical industry as being an "acidic" phenol, though acidic in that case does not have the classic meaning as being acidic in a conventional aqueous system.

The second fundamental approach to develop a calibrated method for organic matrices based on conventional pH methods and instruments is a direct measurement of the voltage generated by a standard hydrogen electrode, also known as a "pH probe." A pH probe measures the liquid junction potential between the sample of interest and the electrode's electrolyte laden filling reference solution, and double-junction reference electrodes are also well known in the art. Typical electrolytes employed with the reference solution include potassium chloride and other organic or inorganic salts. In conventional pH methods and instruments, the matrix being measured and the reference solution are aqueous, however, when the matrix being measured is organic, the reference solution is also organic, typically of very similar materials as the organix matrix and comprising an appropriate organic salt, and optionally a minor amount of water. Again, the voltage value that will be provided by such a pH probe in an organic matrix with an organic reference solution cannot be generally and directly translated to hydrogen activity and acid and base concentration as is often the case with an aqueous matrix, but rather has been specifically correlated to some property of the organic matrix of interest, such as the concentration of an acid catalyst or a basic material.

There are permutations and combinations of these fundamental approaches, for example, using a pH probe on a diluted aliquot of organic sample.

In any approach to developing a calibrated method for determining of the amount of basic material or acid catalyst in an organic matrix, the reading or measurement value only has meaning when the instrument and method employed has been specifically correlated to the property of interest. For example, with regard to a pH probe, one may consult U.S. Pat. No. 5,066,373, wherein a titration curve for a double-junction reference electrode pH probe is developed based on adding known amounts of acid and base to an organic matrix of phenol, acetone and cumene; the reference solutions comprise a suitable organic matrix of phenol, acetone and cumene, and an electrolyte of a tetralkyl- or a tetraarylammonium salt. The titration curve is developed by recording the voltage generated by the pH probe at various concentrations of acid and base, generally by starting with an organic matrix free of either and assigning the voltage measured as "neutral," that is, comprising no or virtually no unreacted or uncomplexed specie of acid catalyst or basic material. Then acid is added in increments to the neutral organic matrix and the voltage recorded, and such voltages and correlated to discrete, precise concentrations of acid. Such voltages may arbitrarily be assigned a lower pH value, though again, this is not pH in the classic definition in aqueous systems. Then base is added to the acidic organic matrix (the organic matrix is titrated) in increments and the voltage recorded, and such voltages are correlated to discrete, precise concentrations of acid with respect to the previously obtained voltages until the voltage passes through the neutral point. Base is then added beyond the neutral point and the voltage recorded and such voltages and correlated to discrete, precise concentrations of base. Such voltages may arbitrarily be assigned a higher pH value, though once again, this is not pH in the classic definition in aqueous systems.

In the instant invention, a calibrated method of determining the amount of acid catalyst or basic material in the treated cleavage reaction mixture may developed. This may involve either fundamental approach to methods and instruments discussed herein, wherein a titration curve is developed to correlate a specific, measured pH value (for example using pH paper on a diluted aliquot of organic sample), or voltage measurement (for example using a pH probe on an undiluted sample of organic matrix), to a specific amount of acid catalyst or basic material in a treated cleavage reaction mixture. Typically the titration curve will be developed with an organic matrix comprising cyclohexylbenzene, phenol and cyclohexanone. In one specific embodiment, the starting organic matrix for developing the titration curve for a calibrated method comprises 80 wt % cyclohexylbenzene, 10 wt % phenol and 10 wt % cyclohexanone. Such a starting organic matrix, if used as a reference solution in a double-junction pH probe, may further comprise a suitable electrolyte, such as 0.02 wt % or 0.03 wt % of a tetraalkyl- or tetrarlyammonium salt, such as tetraphenylammonium chloride or tetramethylammonium bromide, and optionally a minor amount of water, say 1 wt %, these percentages being with respect to the overall mixture (the organic matrix percentage figures should maintain the aforementioned proportions though their absolute value may be reduced somewhat by the salt or the water).

The calibrated method of choice to determine the amount of acid catalyst or basic material in the treated cleavage reaction mixture may be employed in this invention on a continual basis, that is, determined periodically on a regular frequency. Direct (undiluted) measurements using pH probes are convenient for such continual determination, and this may even be employed continuously to provide an analog signal of voltage. However, diluted approaches of various types will also suffice to allow continual determination on a useful frequency. In one embodiment, the continually determined amount of the acid catalyst and basic material in the treated cleavage reaction mixture can continually be compared to a target amount, and a difference between the determined and target amount similarly continually determined The introduction of basic material to the cleavage reaction mixture can then be adjusted appropriately based on this continually determined difference to reduce the difference and more closely approach the target amount of acid catalyst and basic material. This continual determination and adjustment may be conducted with a suitable automated control system, wherein a computer (i) receives a signal from a calibrated method instrument that it correlates to an amount of acid and base in the treated cleavage reaction mixture, (ii) calculates the difference based on a manually input target amount, and (iii) for example, should the difference value indicates there is more acid than the target amount, increases the introduction of basic material by an amount proportional to the difference via increasing the opening of a control valve in a line that introduces basic material.

In various embodiments, contacting the basic material and the at least a portion of the cleavage reaction mixture is conducted in a reactor, the neutralization reactor. The neutralization reactor may be any vessel that allows contacting of the acid catalyst with a basic material for a suitable residence time. For example, the neutralization reactor may be an open or substantially open vessel reactor or pipe. The neutralization reaction is exothermic, but generally the amount of acid catalyst and basic material reacting is small relative to the overall amount of treated cleavage reaction mixture, and heat management is not a particular concern for the neutralization reactor.

In various embodiments, contacting the basic material and the at least a portion of the cleavage reaction mixture in the neutralization reactor occurs for a suitable residence time to enable stoichiometric or near stoichiometric conversion of the acid catalyst and basic material species, according the prevailing chemical kinetics of the acid catalyst and basic material species at the neutralization conditions employed in the present invention. In various embodiments, the residence time is at least 0.01 and no greater than 30 minutes, or at least 0.05 and no greater than 20 minutes, or at least 1 and no greater than 5 minutes.

At least a portion of the treated cleavage reaction mixture may be subjected to a processing, which may include all or some fraction of the treated cleavage reaction mixture as directly produced without undergoing any separation (e.g., some fraction resulting from diverting some amount of the treated cleavage reaction mixture as directly produced to another disposition, such as temporary storage). Thus, the at least a portion of the treated cleavage reaction mixture may have the same composition as the treated cleavage reaction mixture. Further, all or some of the treated cleavage reaction mixture as directly produced may undergo one or more separations, and an appropriate product of that separation (or separations), now modified in composition relative the treated cleavage reaction mixture as directly produced, may provide the at least a portion of the treated cleavage reaction mixture subjected to the neutralization reaction.

In various embodiments, the invention relates to: (a) oxidizing at least a portion of a feed comprising cyclohexylbenzene to produce an oxidation composition comprising cyclohexyl-1-phenyl-1-hydroperoxide; (b) cleaving at least a portion of the oxidation composition in the presence of an acid catalyst to produce a cleavage reaction mixture comprising the acid catalyst, phenol and cyclohexanone; and (c) neutralizing at least a portion of the cleavage reaction mixture with a basic material to form a treated cleavage reaction mixture. It will be understood by one skilled in the art that the oxidation composition may undergo one or more actions between (a) and (b) that alter the composition. For example, one or more feed streams and/or recycle streams may be added to the oxidation composition. Additionally or alternatively, one or more separations and/or purifications may be performed on the oxidation composition. It is intended that such altered compositions be included within the definition of "oxidation composition."

Similarly, the cleavage reaction mixture may undergo one or more actions between (b) and (c) that alter the composition. It is intended that such altered compositions be included within the definition of "cleavage reaction mixture."

Processing of Treated Cleavage Reaction Mixture

In various embodiments of the present invention, at least a portion of the treated cleavage reaction mixture is separated into a product that enriched in phenol, or cyclohexanone, or cyclohexylbenzene, or any combination thereof relative to the amount of phenol, or cyclohexanone, or cyclohexylbenzene, or any combination in at least a portion of the treated cleavage reaction mixture, and depleted in neutralization complexation product relative to the at least a portion of the treated cleavage reaction mixture.

In one specific embodiment, at least a portion of the treated cleavage reaction mixture is subjected to one or more fractional distillation steps to produce a bottoms material that comprises no greater than 5 wt % of cyclohexylbenzene, phenol and cyclohexanone combined, that wt % being based on the total weight of the bottoms material, and further contains at least 95 wt % of the complexation product contained in the at least a portion of the treated cleavage reaction mixture subjected to fractional distillation, that wt % based upon the total weight of the at least a portion of the treated cleavage reaction mixture subjected to fractional distillation. (Thus, the amount of complexation product in the bottoms stream may be less and considerably less than 95 wt % based on the total weight of the bottoms stream. In other words, it is convenient to recover in this bottoms stream a high proportion of the complexation product found in the at least a portion of the treated cleavage reaction mixture, regardless of the resultant proportion of complexation product in the bottoms stream.)

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid and/or plasticizers.

Description According to the Figures

Figure 1:
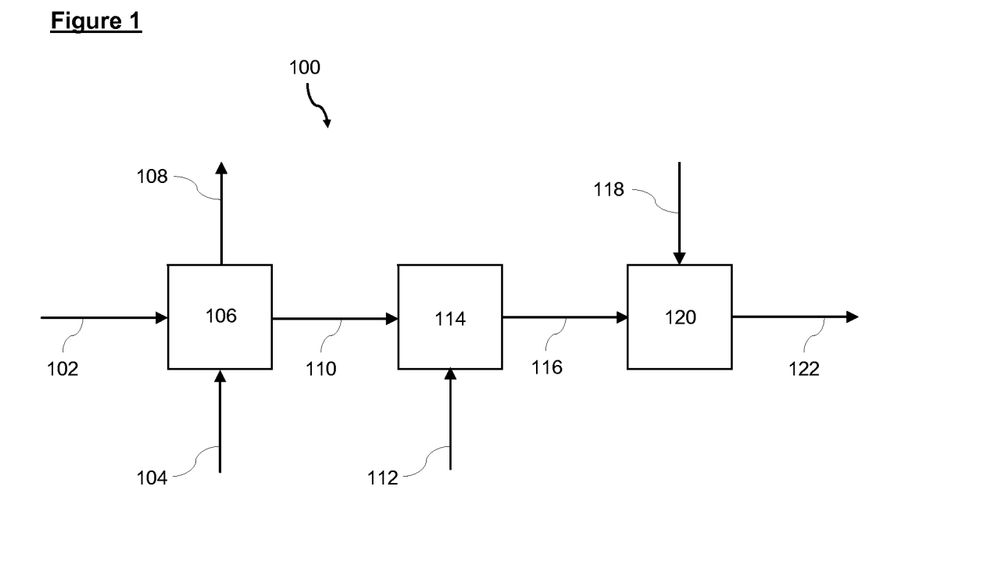
FIG. 1 is a flow diagram of a process for producing phenol that includes treatment of an acid catalyst.

FIG. 1 illustrates an exemplary process 100 for producing phenol and cyclohexanone according to the present invention. The feed comprising cyclohexylbenzene in line 102 is provided to oxidation reactor 106. Oxygen in line 104, conveniently in the form of air, is provided to oxidation reactor 106, and thereby oxygen is introduced to the feed comprising cyclohexylbenzene. The oxygen in line 104 may also be derived from air, for example, air that has been compressed and filtered to remove particulates, air that has been compressed and cooled to condense and remove water, or a stream that has been enriched in oxygen above the natural approximately 21 mol % in air through membrane enrichment of air, cryogenic separation of air or other means within the ken of the skilled artisan.

Continuing with FIG. 1, conditions within oxidation reactor 106 are such that an oxidation reaction occurs, and an oxidation composition comprising cyclohexyl-1-phenyl-1-hydroperoxide is formed. Conveniently, conditions are selected to favor the formation of cyclohexyl-1-phenyl-1-hydroperoxide in the oxidation composition well above other hydroperoxides and dihydroperoxides discussed herein. In one particular embodiment, N-hydroxyphthalimide (NHPI) is also introduced to oxidation reactor 106, by means not shown in FIG. 1, to enhance selectivity to cyclohexyl-1-phenyl-1-hydroperoxide.

As the oxidation reaction continues, oxygen is depleted and an oxygen depleted stream in line 108 is removed from oxidation reactor 106. When the oxygen in line 104 is in the form of air, the oxygen depleted stream in line 108 is typically enriched in nitrogen. When the oxidation reaction is conducted at or near atmospheric pressure, the oxygen depleted stream in line 108 may also contain lower volatility byproducts of the oxidation reaction, such as water, along with minor amounts of cyclohexylbenzene, among other components that may be vapor under the conditions in oxidation reactor 106. In an operation not shown in FIG. 1, the oxygen depleted stream in line 108 may be further processed to recover the cyclohexylbenzene, remove water, and otherwise make the cyclohexylbenzene fit for recycle as feed to oxidation reactor 106, and make other streams suitable for other uses or disposal.

Remaining with FIG. 1, at least a portion of the oxidation composition is withdrawn from oxidation reactor 106 in line 110, including cyclohexyl-1-phenyl-1-hydroperoxide but potentially including other hydroperoxides and dihydroperoxides. In an embodiment where NHPI is introduced to oxidation reactor 106, the oxidation composition including cyclohexyl-1-phenyl-1-hydroperoxide may contain NHPI.

At least a portion of the oxidation composition including cyclohexyl-1-phenyl-1-hydroperoxide in line 110, along with an acid catalyst in line 112, is provided to cleavage reactor 114, and thereby an acid catalyst is introduced to at least a portion of the oxidation composition. In one embodiment, the acid catalyst in line 112 is sulfuric acid or a mixture of sulfuric acid and water. Conditions in cleavage reactor 114 are such that a cleavage reaction occurs, causing cyclohexyl-1-phenyl-1-hydroperoxide but also any other hydroperoxides and dihydroperoxides present, to decompose to materials such as phenol, cyclohexanone and form a cleavage reaction mixture. At least a portion of the cleavage reaction mixture including phenol, cyclohexanone, and the acid catalyst is withdrawn from cleavage reactor 114 in line 116. Potentially, the at least a portion of the cleavage reaction mixture in line 116 may also contain a contaminant.

Still with FIG. 1, the at least a portion of cleavage reaction mixture in line 116, and a basic material in line 118, are directed to a neutralization reactor 120, and thereby a basic material is introduced to at least a portion of the cleavage reaction mixture. In one embodiment, the basic material in line 118 is an amine or diamine, such as 2-methylpentane-1,5-diamine (DYTEK™ A). Conditions within neutralization reactor 120 are such that a neutralization reaction occurs of at least a portion of the basic material and at least a portion of the acid catalyst in the at least a portion of the cleavage reaction mixture, and a treated cleavage reaction mixture is formed. A treated cleavage reaction mixture in line 122 is removed from neutralization reactor 120, conveniently having a reduced content of acid catalyst compared to that in the at least a portion of the cleavage reaction mixture in line 116, and conveniently comprising a complexation product. In another embodiment not shown in FIG. 1, at least a portion of the treated cleavage reaction mixture may be subjected to further processing to, for example, further purify phenol and cyclohexanone, separate phenol from cyclohexanone, and the like.

In another embodiment not shown in FIG. 1, the basic material may be a liquid aqueous base, for example aqueous sodium hydroxide, and neutralization reactor 120 may be a continuous countercurrent wash column, or a liquid-liquid extraction column or countercurrent series of liquid-liquid contacting drums. In such an embodiment, a line not shown in FIG. 1 may be present carrying the fresh liquid basic material into and the used liquid basic material out of neutralization reactor 120. Conveniently, the used liquid basic material will also contain a large proportion or virtually all of any complexation product formed.

In a further embodiment not depicted by FIG. 1, no basic material in line 118 is provided to neutralization reactor 120, rather, the basic material is a solid, for example an ion exchange resin or a solid sodium carbonate. In this instance, the neutralization reactor 120 is a vessel filled with the solid in a manner conducive to fixing the solid in the vessel as the cleavage reaction mixture including an acid catalyst flows over it, and the vessel dimensions and quantity of solid is such as to provide the desired contacting residence time at the given neutralization conditions. Any complexation product formed may be affixed to the solid basic material and remain in neutralization reactor 120, and the solid basic material may be used until it loses effectiveness and then replaced in an appropriate manner.

Figure 2:
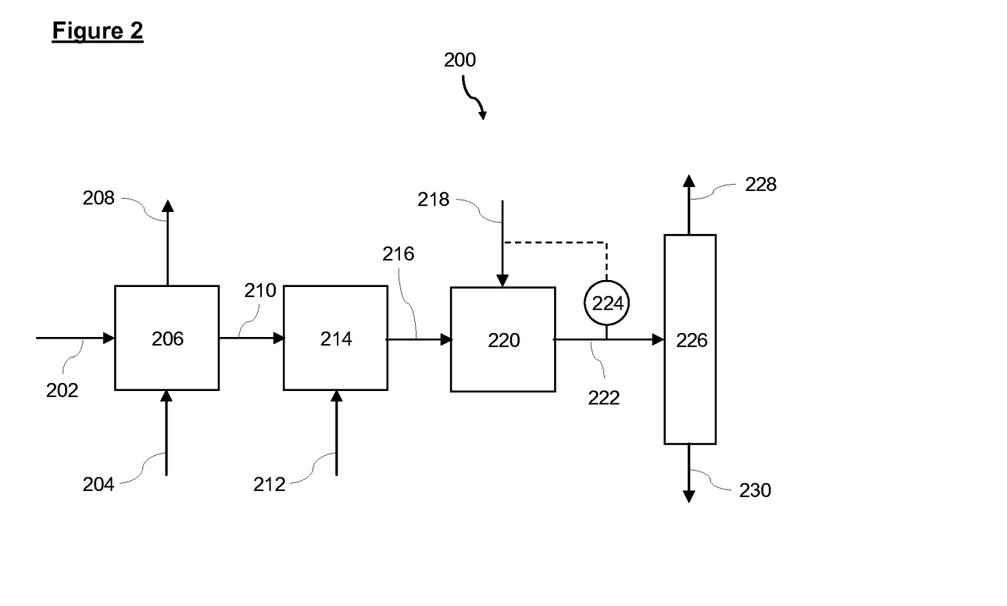
FIG. 2 is a flow diagram of a process for producing phenol that includes a method for measuring basic material content.

Referring now to FIG. 2, there is illustrated another exemplary process 200 for producing phenol and cyclohexanone according to the present invention. The feed comprising cyclohexylbenzene in line 202 is provided to oxidation reactor 206. Oxygen in line 204, conveniently in the form of air, is provided to oxidation reactor 206, and thereby oxygen is introduced to the feed comprising cyclohexylbenzene.

Continuing with FIG. 2, conditions within oxidation reactor 206 are such that an oxidation reaction occurs, and producing a oxidation composition comprising cyclohexyl-1-phenyl-1-hydroperoxide. As the oxidation reaction continues, oxygen is depleted and an oxygen depleted stream in line 208 is removed from oxidation reactor 206.

Remaining with FIG. 2, at least a portion of the oxidation composition including cyclohexyl-1-phenyl-1-hydroperoxide is withdrawn from oxidation reactor 206 in line 210, including cyclohexyl-1-phenyl-1-hydroperoxide but potentially including other hydroperoxides and dihydroperoxides. In an embodiment where NHPI is introduced to oxidation reactor 206, the oxidation reaction product including cyclohexyl-1-phenyl-1-hydroperoxide may contain NHPI.

At least a portion of the oxidation composition including cyclohexyl-1-phenyl-1-hydroperoxide in line 210, along with an acid catalyst in line 212, is provided to cleavage reactor 214, and thereby an acid catalyst is introduced to at least a portion of the oxidation composition. In this embodiment according to FIG. 2, the acid catalyst in line 212 is sulfuric acid or a mixture of sulfuric acid and water. Conditions in cleavage reactor 214 are such that a cleavage reaction occurs, causing cyclohexyl-1-phenyl-1-hydroperoxide but also any other hydroperoxides and dihydroperoxides present, to decompose to materials such as phenol, cyclohexanone and form a cleavage reaction mixture. At least a portion of the cleavage reaction mixture including phenol, cyclohexanone, and the acid catalyst is withdrawn from cleavage reactor 214 in line 216. Potentially, the at least a portion of the cleavage reaction mixture in line 216 may also contain a contaminant.

The at least a portion of the cleavage reaction mixture including phenol, cyclohexanone, and an acid catalyst in line 216, and a basic material in line 218, are directed to a neutralization reactor 220, thereby introducing a basic material to at least a portion of a cleavage reaction mixture. In this embodiment according to FIG. 2, the basic material in line 218 is a relatively high molecular weight amine, 2-methylpentane-1,5-diamine. Conditions within neutralization reactor 220 are such that a neutralization reaction takes place wherein the at least a portion of the diamine complexes with and neutralizes at least a portion of the sulfuric acid in the at least a portion of the cleavage reaction mixture in line 216, creating a treated cleavage reaction mixture. The cleavage reaction mixture comprises phenol, cyclohexanone, cyclohexylbenzene, and amine-sulfuric acid complexation product. The amine-sulfuric acid complexation product is completely soluble in the treated cleavage reaction mixture, and further has a relatively low volatility compared to cyclohexylbenzene. At least a portion of the treated cleavage reaction mixture is removed from neutralization device 220 in line 222.

Still with FIG. 2, the at least a portion of treated cleavage reaction mixture in line 222 is exposed to a measurement and control device 224 that uses a calibrated method to continually determine the amount of acid catalyst or basic material in the at least a portion of the treated cleavage reaction mixture. The calibrated method has been developed using techniques described earlier, in this embodiment according to FIG. 2, specifically directed to sulfuric acid and 2-methylpentane-1,5-diamine (DYTEK™ A). Conveniently, the measurement and control device 224 also continually determines the amount of acid catalyst or basic material in the at least a portion of treated cleavage reaction mixture in line 222, continually determines a difference between the continually determined amount of acid catalyst or basic material and a target amount of acid catalyst or basic material in the at least a portion of treated cleavage reaction mixture, and adjusts the rate of introduction of basic material in line 218 as needed to more closely approach the target amount of acid catalyst or basic material. The adjustment may take place by sending an electronic signal, represented by the dashed line attached to measurement and control device 224, to an element such as a control valve associated with the basic material in line 218, not shown in FIG. 1, that will increase or decrease the introduction of the basic material by an amount as may be correlated with the difference between the continually determined amount of acid catalyst or basic material and the target amount of acid catalyst or basic material in the at least a portion of treated cleavage reaction mixture.

Keeping with FIG. 2, the at least a portion of the treated cleavage reaction mixture in line 222, having near the target amount of acid catalyst or basic material and comprising a complexation product, is provided to fractionation column 226. Fractionation column 226 is operated to provide an overhead product in line 228 that is enriched in cyclohexylbenzene and components with a higher volatility than cyclohexylbenzene relative to the at least a portion of the treated cleavage reaction mixture in line 222, and depleted of components having a lower volatility than cyclohexylbenzene, particularly a complexation product, relative to the at least a portion of the treated cleavage reaction mixture in line 222. Fractionation column 224 is also operated to provide a converse bottoms product in line 230 that is depleted in components having a lower volatility than cyclohexylbenzene relative to the at least a portion of the treated cleavage reaction mixture in line 222, and enriched in cyclohexylbenzene, and components having a higher volatility than cyclohexylbenzene, relative to the at least a portion of the treated cleavage reaction mixture in line 222. Further, the bottoms product in line 230 conveniently contains most, potentially all, of the amine-sulfuric acid complexation product introduced to fractionation column 224 in the at least a portion of the treated cleavage reaction mixture in line 222.

EXAMPLES

The invention will now be more particularly described with reference to the following non-limiting Examples.

Example 1

Oxidation of Cyclohexylbenzene using NHPI Catalyst

One hundred fifty (150) grams of cyclohexylbenzene and 0.16 grams of NHPI, both purchased from TCI America, Inc., were weighed into a Parr reactor fitted with a stirrer, thermocouple, gas inlet, sampling port and a condenser containing a Dean Stark trap for water removal. The reactor contents were stirred at 1000 revolutions-per-minute (rpm) and sparged with nitrogen at a flow rate of 225 cm$^3$/minute for 5 minutes. The reactor was maintained under a nitrogen sparge and heated to a reaction temperature of 110° C. The sparge gas was switched to air and sparged at 250 cm$^3$/minute for four (4) hours. Samples of the oxidation composition in the Parr reactor were taken hourly and analyzed by gas chromatography (GC). After four (4) hours, the gas was switched back to nitrogen and the heat was turned off.

Example 2

Neutralization of Cleavage Reaction Mixture using Sodium Carbonate

The oxidation composition generated in Example 1 was mixed with approximately 8 wt % decane and charged into a glass flask maintained at 53° C. 0.5 mL of 1.5 wt % sulfuric acid catalyst in nitromethane were added to the flask, giving a sulfuric acid concentration of 1500 wppm in the cleavage reaction mixture. The cleavage reaction occurred instantaneously as indicated by the reaction exotherm to form the cleavage products. An aliquot of the cleavage reaction mixture was taken after 10 minutes and the sulfuric acid was neutralized using a stoichiometric amount of 10 wt % sodium carbonate solution to form the treated cleavage reaction mixture. The sample was analyzed using GC and the composition results of the oxidation composition and treated cleavage reaction mixture are listed in Table 1.

TABLE 1

| Component | Oxidation Composition (wt %) | Treated cleavage reaction mixture (wt %) |
|---|---|---|
| Light Oxygenates | 0.078 | 0.166 |
| Cyclohexanone | 0.028 | 6.873 |
| Phenol | 0.022 | 7.016 |
| Decane | 8.952 | 8.798 |
| Other C12 | 0.411 | 0.436 |
| Cyclohexylbenzene | 7005 | 72.102 |
| Phenylcyclohexenes | 0.205 | 1.329 |
| Phenylcyclohexanols | 2.527 | 0.754 |
| Phenylcyclohexanones | 0.553 | 0.669 |
| Cyclohexyl-1-phenyl-1-hydroperoxide | 16.416 | 0.134 |
| Other hydroperoxides | 0.660 | 0.420 |
| Other Oxygenates | 1.067 | 1.102 |
| C18 | 0.175 | 0.150 |
| Hydroperoxide Conversion (%) | — | 99.2 |
| Cyclohexanone Yield (%) | — | 79.6 |
| Phenol Yield (%) | — | 84.8 |

Example 3

Neutralization of Cleavage Reaction Mixture using Hexamethyleneimine

An oxidation composition made in a manner similar to that described in Example 1 was mixed with approximately 8 wt % decane and charged into a glass flask maintained at 62° C. 0.5 mL of 1.5 wt % sulfuric acid in nitromethane were added to the flask, giving a sulfuric acid catalyst concentration of 1500 wppm in the cleavage reaction mixture. The cleavage reaction occurred instantaneously as indicated by the reaction exotherm to form the cleavage products. An aliquot of the cleavage reaction mixture was taken after 10 minutes and sulfuric acid was neutralized using a stoichiometric amount of 1 M hexamethyleneimine solution in nitromethane to form the treated cleavage reaction mixture. The treated cleavage reaction mixture was analyzed using GC and the composition results of the oxidation composition and treated cleavage reaction mixture are listed in Table 2.

TABLE 2

| Component | Oxidation Composition (wt %) | Treated cleavage reaction mixture (wt %) |
|---|---|---|
| Light Oxygenates | 0.062 | 0.029 |
| Cyclohexanone | 0.030 | 5.575 |
| Phenol | 0.023 | 5.981 |
| Decane | 8.319 | 8.239 |
| Other C12 | 0.410 | 0.430 |
| Cyclohexylbenzene | 71.640 | 74.943 |
| Phenylcyclohexenes | 0.191 | 1.415 |
| Phenylcyclohexanols | 2.368 | 0.764 |

TABLE 2-continued

| Component | Oxidation Composition (wt %) | Treated cleavage reaction mixture (wt %) |
|---|---|---|
| Phenylcyclohexanones | 0.527 | 0.785 |
| Cyclohexyl-1-phenyl-1-hydroperoxide | 14.614 | 0.137 |
| Other hydroperoxides | 0.684 | 0.205 |
| Other oxygenates | 0.928 | 1.291 |
| C18 | 0.184 | 0.161 |
| Hydroperoxide Conversion (%) | — | 99.0 |
| Cyclohexanone Yield (%) | — | 81.6 |
| Phenol Yield (%) | — | 91.2 |

Example 4

Neutralization of Cleavage Reaction Mixture using 2,6-diisopropylaniline

An oxidation composition made in accordance with Example 1 was mixed with 8 wt % decane and loaded into a pump and fed at a rate of 3.33 cm$^3$/min into a 50-mL glass continuously-stirred tank reactor (CSTR) held at 64° C. Concentrated sulfuric acid catalyst was added to the reactor to keep the sulfuric acid concentration at 3,000 wppm in the cleavage reaction mixture. The cleavage reaction occurred instantaneously as indicated by the reaction exotherm to form the cleavage reaction mixture. An aliquot of the cleavage reaction mixture was taken after 10 minutes and the sulfuric acid catalyst was neutralized using a stoichiometric amount of 2,6-diisopropylaniline to form the treated cleavage reaction mixture. The treated cleavage reaction mixture was analyzed using GC and the composition results of the oxidation composition and treated cleavage reaction mixture are listed in Table 3.

TABLE 3

| Component | Oxidation Composition (wt %) | Treated cleavage reaction mixture (wt %) |
|---|---|---|
| Cyclohexanone | 0.027 | 5.854 |
| Phenol | 0.015 | 6.681 |
| Decane | 8.827 | 9.168 |
| Other C12 | 0.472 | 0.477 |
| Cyclohexylbenzene | 71.852 | 72.828 |
| Phenyl-1-cyclohexene | 0.049 | 1.340 |
| Phenylcyclohexanols | 0.913 | 0.606 |
| Phenyl-3-cyclohexene | 0.012 | 0.067 |
| Phenylcyclohexanones | 0.191 | 0.673 |
| Cyclohexyl-1-phenyl-1-hydroperoxide | 15.643 | 0.486 |
| Other hydroperoxides | 1.050 | 0.322 |
| Other oxygenates | 0.612 | 0.750 |
| C18 | 0.328 | 0.332 |
| 2,6-diisopropylaniline condensation products | — | 0.409 |
| Hydroperoxide Conversion (%) | — | 97.0 |
| Cyclohexanone Yield (%) | — | 72.8 |
| Phenol Yield (%) | — | 86.6 |

As will be understood by those skilled in the art, the methods of the present invention may utilize numerous equipment and unit operation elements not shown in the Figures or discussed in their description, including but not limited to, heat exchangers through which streams may pass to decrease or increase their temperatures prior to being introduced into another element, as well as pumps and compressors to provide motive force for streams, mixers, instrumentation and control valves.

In addition, although the Figures illustrate continuous processes, batch operations (e.g., with intermittent introduction and removal of streams), or semi-batch operations (e.g., with some streams are intermittently introduced and removed and some streams are continuously removed) are within the scope of the present invention.

Additionally or alternately, the invention can be described by the following embodiments:

1. A process for producing phenol comprising:
   (a) oxidizing at least a portion of a feed comprising cyclohexylbenzene to produce an oxidation composition comprising cyclohexyl-1-phenyl-1-hydroperoxide;
   (b) cleaving at least a portion of the oxidation composition in the presence of an acid catalyst to produce a cleavage reaction mixture comprising the acid catalyst, phenol and cyclohexanone; and
   (c) neutralizing at least a portion of the cleavage reaction mixture with a basic material to form a treated cleavage reaction mixture, wherein the treated cleavage reaction mixture contains no greater than 50 weight-parts-per-million (wppm) of the acid catalyst or no greater than 50 wppm of the basic material.
2. The process of embodiment 1, wherein the oxidation composition comprises at least 65 wt % cyclohexylbenzene, the wt % based upon the total weight of the oxidation composition.
3. The process of embodiment 1, wherein the oxidation composition further comprises one or more hydroperoxides selected from cyclohexyl-1-phenyl-2-hydroperoxide; cyclohexyl-1-phenyl-3-hydroperoxide; cyclohexyl-1-phenyl-4-hydroperoxide; cyclopentyl-1-methyl-2-phenyl-2-hydroperoxide; cyclopentyl-1-methyl-3-phenyl-3-hydroperoxide; cyclopentyl-1-methyl-1-phenyl-2-hydroperoxide; cyclopentyl-1-methyl-1-phenyl-3-hydroperoxide; cyclohexyl-1-phenyl-1,2-dihydroperoxide; cyclohexyl-1-phenyl-1,3-dihydroperoxide; cyclohexyl-1-phenyl-1,4-dihydroperoxide; cyclopentyl-1-methyl-2-phenyl-1,2-dihydroperoxide; cyclopentyl-1-methyl-2-phenyl-2,3-dihydroperoxide; cyclopentyl-1-methyl-2-phenyl-2,4-dihydroperoxide; and cyclopentyl-1-methyl-2-phenyl-2,5-dihydroperoxide.
4. The process of embodiment 1, wherein the acid catalyst is one or more of sulfuric acid, perchloric acid, phosphoric acid, hydrochloric acid and p-toluene sulfonic acid.
5. The process of embodiment 1, wherein the cleavage reaction mixture comprises at least 50 wppm and no greater than 3000 wppm of the acid catalyst, based upon total weight of the cleavage reaction mixture.
6. The process of embodiment 1, wherein the basic material is one or more of ammonia, ammonium hydroxide, an alkali metal hydroxide, a basic clay, an anionic exchange resin, an activated carbon and an amine.
7. The process of embodiment 1, wherein the basic material is an aliphatic amine.
8. The process of embodiment 1, wherein the basic material is a diamine.
9. The process of embodiment 1, wherein the neutralizing in (c) occurs at a temperature of at least 30° C. and no greater than 200° C., and a pressure of at least 5 and no greater than 3450 kPa.
10. The process of embodiment 9, wherein the neutralizing in (c) occurs at a temperature of at least 40° C. and no greater than 150° C. and a pressure of at least 70 and no greater than 1380 kPa.

11. The process of embodiment 1, wherein the treated cleavage reaction mixture contains no greater than 25 wppm of the acid catalyst and no greater than 25 wppm of the basic material.

12. The process of embodiment 1, wherein the amount of at least one of the acid catalyst and basic material in the treated cleavage reaction mixture is determined using a calibrated method.

13. The process of embodiment 12, wherein the amount of acid catalyst or basic material in the treated cleavage reaction mixture is determined continually, and the process further includes: (i) continually determining a difference between the continually determined amount of acid catalyst or basic material and a target amount of acid catalyst or basic material in the treated cleavage reaction mixture; and (ii) adjusting the amount of basic material in (c) on the basis of the continually determined difference to approach the target amount of acid catalyst or basic material in the treated cleavage reaction mixture.

14. The process of embodiment 1, wherein the neutralizing of the basic material and acid catalyst in (c) forms a complexation product that is soluble in the treated cleavage reaction mixture, is stable at a temperature of at least 185° C., and has a lower volatility than cyclohexylbenzene.

15. The process of embodiment 1, wherein at least a portion of the treated cleavage reaction mixture is subjected to one or more fractional distillation steps to produce a bottoms material that comprises less than 5 wt % of cyclohexylbenzene, phenol and cyclohexanone combined, that wt % being based on the total weight of the bottoms material, and further contains more than 95 wt % of the complexation product contained in the at least a portion of the treated cleavage reaction mixture subjected to the fractional distillation, that wt % based upon the total weight of the at least a portion of the treated cleavage reaction mixture subjected to the fractional distillation.

16. Phenol produced by the process of 1.

17. Cyclohexanone produced by the process of 1.

18. At least one of a phenolic resin, bisphenol A, ε-caprolactam, an adipic acid or a plasticizer produced from the phenol of 16.

19. At least one of adipic acid, a cyclohexanone resin, a cyclohexanone oxime, caprolactam or nylon produced from the cyclohexanone of 17.

20. A process for producing phenol comprising:
  (a) introducing oxygen to a feed comprising cyclohexylbenzene to cause an oxidation reaction to occur and produce an oxidation composition comprising cyclohexyl-1-phenyl-1-hydroperoxide;
  (b) introducing an acid catalyst to at least a portion of the oxidation composition to cause a cleavage reaction to occur, and produce a cleavage reaction mixture comprising the acid catalyst, phenol and cyclohexanone; and
  (c) introducing a basic material to at least a portion of the cleavage reaction mixture to cause a neutralization reaction to occur of at least a portion of the basic material with at least a portion of the acid catalyst in the at least a portion of cleavage reaction mixture, and form a treated cleavage reaction mixture, wherein the treated cleavage reaction mixture contains no greater than 50 wppm of the acid catalyst or no greater than 50 wppm of the basic material.

21. A process for producing phenol comprising:
  (a) oxidizing cyclohexylbenzene to produce an oxidation composition comprising cyclohexyl-1-phenyl-1-hydroperoxide;
  (b) cleaving at least a portion of the cyclohexyl-1-phenyl-1-hydroperoxide in the presence of an acid catalyst to produce a cleavage reaction mixture comprising the acid catalyst and at least some phenol and cyclohexanone; and
  (c) neutralizing at least some of the acid catalyst from the cleavage reaction mixture with a basic material, thereby forming a treated cleavage reaction mixture, wherein the treated cleavage reaction mixture contains no greater than 50 wppm of the acid catalyst or no greater than 50 wppm of the basic material.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol comprising:
  (a) oxidizing at least a portion of a feed comprising cyclohexylbenzene to produce an oxidation composition comprising cyclohexyl-1-phenyl-1-hydroperoxide;
  (b) cleaving at least a portion of the oxidation composition in the presence of an acid catalyst to produce a cleavage reaction mixture comprising the acid catalyst, phenol and cyclohexanone; and
  (c) neutralizing at least a portion of the cleavage reaction mixture with a basic material to form a treated cleavage reaction mixture, wherein the treated cleavage reaction mixture contains no greater than 50 weight-parts-per-million (wppm) of the acid catalyst or no greater than 50 wppm of the basic material,
  wherein at least a portion of the treated cleavage reaction mixture is subjected to one or more fractional distillation steps to produce a bottoms material that comprises less than 5 wt % of cyclohexybenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the least a portion of the treated cleavage reaction mixture subjected to the fractional distillation.

2. The process of claim 1, wherein the oxidation composition comprises at least 65 wt % cyclohexylbenzene, the wt % based upon the total weight of the oxidation composition.

3. The process of claim 1, wherein the oxidation composition further comprises one or more hydroperoxides selected from cyclohexyl-1-phenyl-2-hydroperoxide; cyclohexyl-1-phenyl-3-hydroperoxide; cyclohexyl-1-phenyl-4-hydroperoxide; cyclopentyl-1-methyl-2-phenyl-2-hydroperoxide; cyclopentyl-1-methyl-3-phenyl-3-hydroperoxide; cyclopentyl-1-methyl-1-phenyl-2-hydroperoxide; cyclopentyl-1-methyl-1-phenyl-3-hydroperoxide; cyclohexyl-1-phenyl-1,2-dihydroperoxide; cyclohexyl-1-phenyl-1,3-dihydroperoxide; cyclohexyl-1-phenyl-1,4-dihydroperoxide; cyclopentyl-1-methyl-2-phenyl-1,2-dihydroperoxide; cyclopentyl-1-methyl-2-phenyl-2,3-dihydroperoxide; cyclopentyl-1-methyl-2-phenyl-2,4-dihydroperoxide; and cyclopentyl-1-methyl-2-phenyl-2,5-dihydroperoxide.

4. The process of claim 1, wherein the acid catalyst is one or more of sulfuric acid, perchloric acid, phosphoric acid, hydrochloric acid and p-toluene sulfonic acid.

5. The process of claim 1, wherein the cleavage reaction mixture comprises at least 50 wppm and no greater than 3000 wppm of the acid catalyst, based upon total weight of the cleavage reaction mixture.

6. The process of claim 1, wherein the basic material is one or more of ammonia, ammonium hydroxide, an alkali metal hydroxide, a basic clay, an anionic exchange resin, an activated carbon and an amine.

7. The process of claim 1, wherein the basic material is an aliphatic amine.

8. The process of claim 1, wherein the basic material is a diamine.

9. The process of claim 1, wherein the neutralizing in (c) occurs at a temperature of at least 30° C. and no greater than 200° C., and a pressure of at least 5 and no greater than 3450 kPa.

10. The process of claim 9, wherein the neutralizing in (c) occurs at a temperature of at least 40° C. and no greater than 150° C. and a pressure of at least 70 and no greater than 1380 kPa.

11. The process of claim 1, wherein the treated cleavage reaction mixture contains no greater than 25 wppm of the acid catalyst and no greater than 25 wppm of the basic material.

12. The process of claim 1, wherein the amount of at least one of the acid catalyst or basic material in the treated cleavage reaction mixture is determined using a calibrated method.

13. The process of claim 12, wherein the amount of acid catalyst or basic material in the treated cleavage reaction mixture is determined continually, and the process further includes: (i) continually determining a difference between the continually determined amount of acid catalyst or basic material and a target amount of acid catalyst or basic material in the treated cleavage reaction mixture; and (ii) adjusting the amount of basic material in (c) on the basis of the continually determined difference to approach the target amount of acid catalyst or basic material in the treated cleavage reaction mixture.

14. The process of claim 1, wherein the complexation product is soluble in the treated cleavage reaction mixture, is stable at a temperature of at least 185° C., and has a lower volatility than cyclohexylbenzene.

15. A process for producing phenol comprising:
(a) introducing oxygen to a feed comprising cyclohexylbenzene to cause an oxidation reaction to occur and produce an oxidation composition comprising cyclohexyl-1-phenyl-1-hydroperoxide;
(b) introducing an acid catalyst to at least a portion of the oxidation composition to cause a cleavage reaction to occur, and produce a cleavage reaction mixture comprising the acid catalyst, phenol and cyclohexanone; and
(c) introducing a basic material to at least a portion of the cleavage reaction mixture to cause a neutralization reaction to occur of at least a portion of the basic material with at least a portion of the acid catalyst in the at least a portion of cleavage reaction mixture, and form a treated cleavage reaction mixture, wherein the treated cleavage reaction mixture contains no greater than 50 wppm of the acid catalyst or no greater than 50 wppm of the basic material,
wherein at least a portion of the treated cleavage reaction mixture is subjected to one or more fractional distillation steps to produce a bottoms material that comprises less than 5 wt % of cyclohexybenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the least a portion of he treated cleavage reaction mixture subjected to the fractional distillation.

16. A process for producing phenol comprising:
(a) oxidizing cyclohexylbenzene to produce an oxidation composition comprising cyclohexyl-1-phenyl-1-hydroperoxide;
(b) cleaving at least a portion of the cyclohexyl-1-phenyl-1-hydroperoxide in the presence of an acid catalyst to produce a cleavage reaction mixture comprising the acid catalyst and at least some phenol and cyclohexanone; and
(c) neutralizing at least some of the acid catalyst from the cleavage reaction mixture with a basic material, thereby forming a treated cleavage reaction mixture, wherein the treated cleavage reaction mixture contains no greater than 50 wppm of the acid catalyst or no greater than 50 wppm of the basic material,
wherein at least a portion of the treated cleavage reaction mixture is subjected to one or more fractional distillation steps to produce a bottoms material that comprises less than 5 wt % of cyclohexybenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the least a portion of he treated cleavage reaction mixture subjected to the fractional distillation.

* * * * *

UNITED STATES PATENT AND TRADEMARK OFFICE
CERTIFICATE OF CORRECTION

PATENT NO. : 9,115,068 B2
APPLICATION NO. : 13/816618
DATED : August 25, 2015
INVENTOR(S) : Keith H. Kuechler et al.

It is certified that error appears in the above-identified patent and that said Letters Patent is hereby corrected as shown below:

In the Claims

At col. 28, lines 20-46, claim 1 is amended to read:

1. A process for producing phenol comprising:
   (a) oxidizing at least a portion of a feed comprising cyclohexylbenzene to produce an oxidation composition comprising cyclohexyl-1-phenyl-1-hydroperoxide;
   (b) cleaving at least a portion of the oxidation composition in the presence of an acid catalyst to produce a cleavage reaction mixture comprising the acid catalyst, phenol and cyclohexanone; and
   (c) neutralizing at least a portion of the cleavage reaction mixture with a basic material to form a treated cleavage reaction mixture, wherein the treated cleavage reaction mixture contains no greater than 50 weight-parts-per-million (wppm) of the acid catalyst or no greater than 50 wppm of the basic material,
   wherein at least a portion of the treated cleavage reaction mixture is subjected to one or more fractional distillation steps to produce a bottoms material that comprises less than 5 wt % of cyclohexylbenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the at least a portion of the treated cleavage reaction mixture subjected to the fractional distillation.

At col. 29, line 42-column 30, line 22, claim 15 is amended to read:

15. A process for producing phenol comprising:
   (a) introducing oxygen to a feed comprising cyclohexylbenzene to cause an oxidation reaction to occur and produce an oxidation composition comprising cyclohexyl-1-phenyl-1-hydroperoxide;
   (b) introducing an acid catalyst to at least a portion of the oxidation composition to cause a cleavage reaction to occur, and produce a cleavage reaction mixture comprising the acid catalyst, phenol and cyclohexanone; and Signed and Sealed this
Third Day of May, 2016

Michelle K. Lee
*Director of the United States Patent and Trademark Office*

(c) introducing a basic material to at least a portion of the cleavage reaction mixture to cause a neutralization reaction to occur of at least a portion of the basic material with at least a portion of the acid catalyst in the at least a portion of cleavage reaction mixture, and form a treated cleavage reaction mixture, wherein the treated cleavage reaction mixture contains no greater than 50 wppm of the acid catalyst or no greater than 50 wppm of the basic material, wherein at least a portion of the treated cleavage reaction mixture is subjected to one or more fractional distillation steps to produce a bottoms material that comprises less than 5 wt % of cyclohexylbenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the at least a portion of the treated cleavage reaction mixture subjected to the fractional distillation.

At col. 30, lines 23-50, claim 16 is amended to read:

16. A process for producing phenol comprising:

(a) oxidizing cyclohexylbenzene to produce an oxidation composition comprising cyclohexyl-1-phenyl-1-hydroperoxide;

(b) cleaving at least a portion of the cyclohexyl-1-phenyl-1-hydroperoxide in the presence of an acid catalyst to produce a cleavage reaction mixture comprising the acid catalyst and at least some phenol and cyclohexanone; and (c) neutralizing at least some of the acid catalyst from the cleavage reaction mixture with a basic material, thereby forming a treated cleavage reaction mixture, wherein the treated cleavage reaction mixture contains no greater than 50 wppm of the acid catalyst or no greater than 50 wppm of the basic material, wherein at least a portion of the treated cleavage reaction mixture is subjected to one or more fractional distillation steps to produce a bottoms material that comprises less than 5 wt % of cyclohexylbenzene, phenol and cyclohexanone combined, that wt % being based on the total weight of the bottoms material, and further contains more than 95 wt % of a complexation product formed in the neutralizing step (c) that is contained in the at least a portion of the treated cleavage reaction mixture subjected to the fractional distillation, that wt % based upon the total weight of the at least a portion of the treated cleavage reaction mixture subjected to the fractional distillation.